United States Patent [19]

Nakamura et al.

[11] 4,087,622
[45] May 2, 1978

[54] METHOD OF PRODUCING VINYL ACETATE

[75] Inventors: Michihiro Nakamura; Yuzuru Fujiwara; Teruo Yasui, all of Kurashiki, Japan

[73] Assignee: Bayer Aktiengesellschaft, Leverkusen, Germany

[21] Appl. No.: 589,619

[22] Filed: Jun. 23, 1975

[30] Foreign Application Priority Data

Jun. 27, 1974 Japan .................................. 49-73713

[51] Int. Cl.² ............................................ C07C 67/05
[52] U.S. Cl. ..................................... 560/245; 252/474
[58] Field of Search .................... 260/497 A; 560/245

[56] References Cited

U.S. PATENT DOCUMENTS

| | | | |
|---|---|---|---|
| 3,631,079 | 12/1971 | Sennewald | 260/497 A |
| 3,670,014 | 6/1972 | Fernholz | 260/497 A |
| 3,743,607 | 7/1973 | Sennewald | 260/497 A |
| 3,761,513 | 9/1973 | Sennewald | 260/497 A |
| 3,830,834 | 8/1974 | Kronig | 260/497 A |
| 3,939,199 | 2/1976 | Fernholz | 260/497 A |

FOREIGN PATENT DOCUMENTS 1,177,515    1/1970    United Kingdom ............ 260/497 A

*Primary Examiner*—James O. Thomas, Jr.
*Assistant Examiner*—Michael L. Shippen
*Attorney, Agent, or Firm*—Burgess, Dinklage & Sprung

[57] ABSTRACT

Vinyl acetate is produced through reaction of ethylene, oxygen and acetic acid in vapor phase employing a catalyst which comprises 0.3 to 3.0 weight % of palladium metal, 0.0157 to 1.8 weight % of gold metal and 1 to 30 weight % of an alkali metal acetate, all based on the weight of the carrier or catalyst support therefor. These components are supported on said carrier or support under such conditions that (1) at least 90% by weight of each of the supported palladium and gold metals is distributed proximate the external surfaces of the carrier particles, extending to depths no greater than about 30% of the radius of each particle as measured from the external surface of each particle to the center of said particle, and (2) the proportion of gold to palladium ranges from about 5 to 60% by weight, based upon the total weight of the gold and palladium.

5 Claims, No Drawings

METHOD OF PRODUCING VINYL ACETATE

BACKGROUND OF THE INVENTION

1. Field of the Invention

This invention relates to a method of producing vinyl acetate through reaction of ethylene, oxygen and acetic acid in vapor phase, employing a catalyst which comprises metallic palladiu, metallic gold and an alkali metal compound, all deposited on a suitable porous carrier or support. The catalyst components, the proportions thereof, as well as their distribution curves within the porous support, must all fall within certain well-defined limits.

2. Description of the Prior Art

It is known in the art to produce vinyl acetate by reacting ethylene, oxygen and acetic acid in gaseous phase and in the presence of a catalyst comprising palladium, gold and an alkali metal acetate supported on certain carrier materials. Generally, such catalyst system exhibits high activity, but the reaction proceeds too rapidly resulting in various deficiencies and disadvantages, depending on the distribution pattern or profile of the catalyst components which are deposited on, and in relation to the carrier. More particularly, when use is made of the known catalyst systems comprising a porous carrier impregnated with palladium and/or gold, the metal components deposited at or about the support interiors or central regions do not contribute signficantly to the reaction mechanism, since the reactants are scarcely able to diffuse into the central or inner regions of the porous network of the catalyst and hence, the reaction occurs substantially only at the outermost or surface regions of the catalyst. Therefore, the catalyst components, in those reactions known in the art, in large part do not contribute to the reaction scheme, resulting in a reduction in catalytic efficiency per unit weight of the catalyst components. Also, there is encountered an economic disadvantage in that the catalyst components at the inner regions of the carrier are only difficultly recovered and reused. Furthermore, the use of a highly active catalyst at times gives rise to side reactions and, therefore, leads to a reduced selectivity for the contemplated reaction product.

On the other hand, a catalyst wherein the palladium metal and/or gold metal has not substantially penetrated into the carrier, but rather bears most of the metallic component deposited on the carrier surface only, displays a limited catalyst life, and does not permit of the production of vinyl acetate in high yield.

SUMMARY OF THE INVENTION

It has now been found according to the present invention that, in the production of vinyl acetate through reaction of ethylene, oxygen and acetic acid in vapor phase, superior results in vis-a-vis those that can be attained utilizing a catalyst wherein most of the catalyst components are deposited at the exterior surface of the carrier, or wherein same have penetrated far into the central regions of the carrier, can be realized by use of the following specific catalyst, comprising: (A) a porous carrier predominantly composed of silica and/or alumina which has a particle radius of about 1.0 to 5.0 mm and a pore volume of 0.1 to 2.0 cc/g and (B) 0.3 to 3.0 weight % of palladium, 0.0157 to 1.8 weight % of gold and 1 to 30 weight % of alkali metal acetate, based on the weight of the carrier, and which are supported on said carrier under such conditions that (1) at least 90% by weight of each of the supported palladium and gold is distributed proximate the external surfaces of the carrier particles, and extending to depths no greater than 30% of the radius of each particle as measured from the external surface of each particle to the center of said particle, and (2) the proportion of gold to palladium ranges from about 5 to 60% by weight based upon the total weight of the gold and palladium.

DETAILED DESCRIPTION OF THE INVENTION

In the present invention which is characterized by the use of the specific catalyst hereinbefore described, one of the most important features is that the deposited palladium and gold on the carrier, respectively in amounts of at least 90% by weight, are distributed within the carrier particle to depths up to 30% of the lengths of the particle radii, as measured from the surface to the center of each particle. The above feature makes it possible for the catalyst to have appreciable surface area for contact between the catalyst components and the gaseous reactants, to display high catalytic activity, and to greatly diminish loss of catalyst components, i.e., palladium and gold, during the reaction, preparation of the catalyst and the treatment thereof. The distribution pattern or distribution profile of the catalyst components can be determined by means of, for example, X-ray microanalyzer. It should be noted that the desired results cannot be obtained when use is made of a catalyst wherein the palladium and gold are supported on the porous carrier such that either or both of the palladium and gold, in amounts of more than 10% thereof, is distributed within the carrier particle to depths exceeding 30% of the particle radius, as measured from the surface to the center of said particle. Particularly, when such a catalyst is used in the production of vinyl acetate, only low catalytic activity and low selectivity are realized.

With further respect to the catalyst to be used in the present invention, another feature resides in the fact that the amount of the supported gold is within the range of 0.0157 to 1.8 weight %, preferably 0.5 to 1.5 weight %, of the weight of the porous carrier, whereby high activity of the catalyst, and a reduced deterioration in catalytic activity over a given period of time, are assured. The percentage of gold metal relative to the combined weight of palladium and gold metals is preferably within the range of about 5 to 60 percent by weight. If the gold content of the catalyst based on the combined weight of palladium and gold metals is less than 5 percent by weight, the initial activity of the catalyst is low and the aging or deactivation with time of the catalyst is correspondingly high. The amount of palladium metal supported on the carrier according to the invention is not as critical as with respect to the gold metal. However, palladium metal in an amount of 0.3 to 3.0% by weight, again based on the weight of the carrier, affords the most satisfactory results. The alkali metal acetate which serves to enhance the catalytic activity may be uniformly distributed throughout the carrier. Accordingly, the catalyst utilized in the present invention is preferably prepared by supporting palladium and gold at the outer radial and surface extremeties of the carrier, and thence depositing the alkali metal acetate throughout said carrier. The alkali metal acetate may, for example, be potassium acetate, sodium acetate, lithium acetate, or the like.

The term "porous carrier" or "support" as used herein and in the claims, is intended to reflect a carrier which has a particle radius of 1.0 to 5.0 mm, a pore volume of 0.1 to 2.0 cc./g. and an internal surface area of 10 to 350 m²/g. If the particle radius is less than 1.0 mm, the pressure drop in the reaction system is substantial so as to give rise to uneven temperatures in the reaction column for production of vinyl acetate. When the particle radius is in excess of 5.0 mm, the catalyst activity is reduced to an unsatisfactory level. The porous carrier to be employed in the present invention should be predominantly composed of silica or alumina. Other carriers, such as, for example, active carbon, do not provide for the production of vinyl acetate.

The porous carrier, preferably, also has a sharp pore size distribution. As a quantitative expression of pore size distribution, the pore radius distribution curve is desirably employed. The pore radius distribution curve is a curve generated by plotting the logarithm, to the base ten, of pore radius ($r$) (log $r$) on the horizontal axis against $\Delta V/\Delta$ (log $r$) [where V is the volume of pores and the $\Delta$ (delta) reflects an infinitesimal change] on the vertical axis. The term "sharp pore size distribution" as used above denotes a pore size distribution such that, assuming that the maximum peak radius in the pore radius distribution curve between 4 and 750 angstrom units is R, the sum of the pore volumes within the pore radius range of 0.5 R to 1.5 R accounts for not less than 60 percent of the total pore volume in the pore radius range of 4 to 750 angstrom units.

The internal surface area, void volume and pore size distribution as referred to or numerically specified in this specification and the claims appended hereto are those measured by the following procedures. The internal surface area can be calculated from the quantity of nitrogen absorbed at the temperature of liquid nitrogen by the BET method. The void volume and pore size distribution can be calculated as follows. For pores less than 40 A in size, the nitrogen adsorption is measured by means of the BET apparatus. The void volume and pore size distribution of 40 A or larger pores can be measured by the mercury pressure impregnation method using a high pressure mercury porosimeter (Carbo-Erba Model 70).

There is no restriction on the shape of the porous carrier. Thus, it may be globular or cylindrical, or a block having no fixed or definite shape. However, the carrier desirably has a particle radius of 1 to 5 millimeters.

The catalyst hereinabove described which is to be employed in the method of this invention can be prepared, for example, by depositing a small amount of a reduced metal compound (a free metal) onto the porous carrier and, then, impregnating the thus-treated carrier with the required amounts of palladium metal, gold metal and alkali metal acetate. In more detail, when a reduced metal compound in an amount of 0.001 to 0.2 weight percent is deposited on a porous carrier, said amount being relative to the total weight of said carrier, and then the required amounts of palladium metal and gold metal, i.e., two of the catalyst components, are further deposited, this procedure results in a major portion of said palladium and gold being deposited and supported at the outermost radial and surface areas of the carrier and that, when compared with the conventional art recognized catalysts, substantial improvements are attained in both catalyst efficiency and catalyst recovery procedures. The porous carrier should first be impregnated with the metal compound in reduced form. If such metal compound is deposited on the carrier but not having been reduced to the free metal, it is impossible to subsequently impregnate the carrier with palladium and gold in such manner that same are deposited only at the outermost radial and surface areas thereof.

The term "reduced metal compound" which appears hereinbefore denotes a metallic compound which has been reduced to the corresponding free metal. Examples of such metal include platinum, palladium, iridium, rhodium, ruthenium, osmium, gold, silver, iron, cobalt, nickel, chromium, manganese, molybdenum, antimony, zinc, copper, tin and the like. The reduced metal compound to be first present on the porous carrier need not necessarily be the palladium metal and/or gold metal which comprise the actual catalyst components, but since the catalyst according to this invention in fact comprises palladium and gold as the actual catalyst components, it is preferred, in consideration of tendencies such as that towards ionization, that the reduced metal compound to be first deposited on the carrier by a noble metal compound. Furthermore, it is more desirable to employ a reduced metal compound having a catalytic activity of its own that a reduced metal compound which has no catalytic activity whatsoever.

It is essential that the concentration of the reduced metal compound to be thus initially present on the porous carrier be in the range of 0.001 to 0.2 percent by weight, based on the total weight of the porous carrier, the preferred range being from 0.01 to 0.1 percent by weight. When the reduced metal compound to be first deposited is palladium metal, it is advisable to ensure that the concentration of the palladium metal to be thus first deposited be within the range of 0.001 to 0.2 percent by weight and, also, be not more than 10 percent of the total amount of the palladium metal that will ultimately be supported. The surface area of the porous carrier after the deposition of reduced metal remains substantially unchanged, as compared with that prior to deposition.

Any optional procedure may be employed for depositing the reduced metal compound on the porous carrier. For example, a procedure that may be generally employed comprises preparing a solution of a salt of the metal to be deposited, immersing the porous carrier therein, drying the carrier to cause the metal salt to precipitate on the carrier and finally reducing the metal salt with a reducing agent such as hydrogen, hydrazine, formalin, formic acid, or the like. An alternative procedure comprises the thermal decomposition of the metal salt on the porous carrier to cause the corresponding oxide to be formed, in situ, and a subsequent reduction of the oxide.

The reaction is desirably conducted at a temperature of about 50° to 250° C. and under a pressure of about atmospheric to 200 atms. Preferably, the reaction temperature ranges from 100° to 200° C. and the reaction pressure is from atmospheric to 10 atms.

The production of vinyl acetate with the specific catalyst according to this invention is advantageous in that the selectivity of the reaction to vinyl acetate is not reduced by any competing side reaction and, therefore, high yields of product are ensured and catalytic activity is much less diminished upon passage of time. Another advantage is that the noble metals, e.g., palladium and gold, can be utilized in much lesser amounts. As still another advantage, the catalyst of this invention gives rise to reduced recovery costs and, therefore, is quite economical. Furthermore, the catalyst to be employed in the practice of this invention is such that the catalyst components are not easily removed, the catalyst has a high mechanical strength, and the catalyst life is long. Thus, the catalyst of this invention is extremely useful for the production of vinyl acetate.

In order to further illustrate the present invention and the advantages thereof, the following specific examples are given, it being understood that the same are intended merely as illustrative and in no wise limitative. Unless otherwise indicated, all parts are by weight.

EXAMPLE 1

A porous carrier was selected, comprising globular alumina (amnufactured by Mizusawa Chemical Co., Ltd.) which had a particle diameter of 3.5 mm, a surface area of 100 $m^2/g$., a pore volume of 0.87 cc./g. and a maximum peak on its pore radius distribution curve at 420 A, and a pore volume corresponding to 89% of the total pore volume within the pore radius range of 4 to 750 A occurring in the pore radius range of 210 to 630 A. Into 50 parts of water containing 0.03 part of concentrated hydrochloric acid, there were dissolved 0.06 parts of palladium chloride and 0.04 parts of tetrachloroauric acid ($HAuCl_4$), followed by the addition of 35 parts of the aforesaid alumina. After the solution was evaporated to dryness on a steam bath, reduction was carried out with hydrazine hydrate. After the reduction reaction, the carrier was washed with water and dried. By the above treatment, based on the alumina, 0.1 weight % of platinum metal and 0.067 weight % of gold metal were deposited on the alumina. Into a solution of 0.3 parts of concentrated hydrochloric acid there were dissolved 1.24 parts of palladium chloride and 0.86 part of tetrachloroauric acid ($HAuCl_4$). To this solution was added the aforesaid alumina onto which the palladium and gold had been previously deposited. Then, the same procedure as outlined above was followed to prepare a palladium-on-alumina catalyst. The catalyst thus obtained contained 2.2 weight % of palladium metal and 1.5 weight % of gold metal. This catalyst was further impregnated with an aqueous solution of potassium acetate and dried. The procedure provided a catalyst with a potassium acetate content of 3.0 weight %.

Analysis of the catalyst with an X-ray microanalyzer revealed that it supported 97.5% of the total amount of palladium and 95.5% of the gold within 0.2 mm of the carrier surface (within 11.4% of the particle radius extending inwardly from its exterior surface).

As a catalyst for the synthesis of vinyl acetate from ethylene, 35 g. of the aforesaid supported catalyst was placed into a hard glass tube 20 mm in inside diameter, which was then immersed in an oil bath at 120° C. Into this tube, there was introduced a gaseous mixture of ethylene, oxygen and acetic acid (80:10:10) at an hourly rate of 32 liters. The output of vinyl acetate was found to be 192 g./l/hour, the production of carbon dioxide gas being 2.2 mole % of vinyl acetate. Over a period of 98 days, no loss in catalytic activity was encountered.

CONTROL EXAMPLE 1

An alumina-supported catalyst was prepared in a single step, using the same carrier as that used in Example 1, and in such a manner that the catalyst would be supporting 2.2 weight % of palladium and 1.5 weight % of gold. Analysis of this catalyst with an X-ray microanalyzer revealed that the amount of palladium deposited at depths of within 0.2 mm from the catalyst surface accounted for only 21.3% of the total amount of palladium, and that the corresponding amount of gold was 18.5%. The above catalyst was further impregnated with an aqueous solution of potassium acetate. Using the resulting catalyst, the palladium distributions of which were outside the specified conditions of this invention, vinyl acetate was synthesized under the same conditions as described in Example 1. The yield of vinyl acetate was 125 g./l/hour (at the activity observed during the second hour), the production of carbon dioxide gas being 3.1 mole % of the vinyl acetate. At the end of 90 days the activity of the catalyst had dropped to 89% of the level observed during the second hour of reaction.

CONTROL EXAMPLE 2

A porous catalyst was selected, comprising globular alumina (manufactured by Mizusawa Chemical Co., Ltd.) which had a particle diameter of 2.9 mm, a pore volume of 2.6 cc./g., a surface area of 165 $m^2/g$., which was outside of the range specified in this invention, and a maximum peak on its pore radius distribution curve at 350 A, with 83% of the total pore volume within the pore radius range of 4 to 750 A occurring in the pore radius range of 175 to 525 A. Using the above porous carrier, a catalyst was prepared which supported 2.0 weight % of palladium metal and 1.6 weight % of gold metal. The above catalyst was further impregnated with an aqueous solution of potassium acetate. Analysis of the resulting catalyst with an X-ray microanalyzer revealed that the amount of palladium deposited at depths within 3.0 mm from the surface of the catalyst was 95% of the total deposited amount of palladium, and that the corresponding ratio of gold was 96%. In the presence of this supported catalyst, vinyl acetate was synthesized under the same conditions as described in Example 1. In this example, the yield of vinyl acetate was 129 g./l/hour, the production of carbon dioxide gas being 2.8 mole % of the vinyl acetate.

CONTROL EXAMPLE 3

A porous carrier was selected, comprising globular activated carbon, completely free of silica and alumina, with a particle diameter of 3.2 mm, a surface area of 250 $m^2/g$., a pore volume of 0.85 cc/g., a maximum peak on its pore radius distribution curve at 270 A, with 84% of the total pore volume within the pore radius range of 4 to 750 A occurring in the pore radius range of 135 to 405 A. From this activated carbon, there was prepared a catalyst supporting 2.3 weight % of palladium metal and 1.6 weight % of gold metal. The above catalyst was further impregnated with an aqueous solution of potassium acetate. Analysis of the resulting catalyst revealed that the amounts of palladium and gold deposited at depths within 0.3 mm from the surface of the catalyst were 97% and 96% of the respective totals. In the presence of this catalyst, vinyl acetate was synthesized under the same conditions as described in Example 1. In this example, the yield of vinyl acetate was 112 g./l/hour, with the production of carbon dioxide gas being 2.5 mole % of the vinyl acetate.

EXAMPLE 2

The procedure of Example 1 was repeated to prepare catalysts by a two-step method using the same porous carrier as that used in Example 1 (provided that this carrier had a pore volume of 1.22 cc., and a maximum peak on its pore radius distribution curve at 450 A, with 83% of the total pore volume within the pore radius range of 4 to 750 A occurring in the pore radius range of 225 to 675 A) except that $NaAuCl_4$ was used in place of $HAuCl_4$ and the proportions of palladium and gold were varied. The distribution patterns of the palladium and gold are set forth in the following Table I.

Table I

| Weight % of deposit (based on carrier) | | Distribution* | |
|---|---|---|---|
| Palladium | Gold | Palladium | Gold |

| | | | | | | |
|---|---|---|---|---|---|---|
| 4-1 (control) | 1.0 | 0.03 | 6 % | 6 % | | |
| 4-2 | 1.0 | 0.25 | 6 % | 8 % | | |
| 4-3 | 1.0 | 0.43 | 7 % | 9 % | | |
| 4-4 | 1.0 | 0.67 | 9 % | 12 % | | |
| 4-5 | 1.0 | 1.0 | 12 % | 13 % | | |
| 4-6 | 1.0 | 1.5 | 12 % | 15 % | | |
| 4-7 (control) | 1.0 | 2.3 | 16 % | 22 % | | |

*The zone in which 90% of the palladium or gold deposited is present, is expressed as a percent of the radius of the catalyst particle as measured from the external surface of the particle.

A 35 g. portion of each of these catalysts was placed in a hard glass tube which was then immersed in an oil bath at a temperature of 110° C.

A gaseous mixture of ethylene, oxygen and acetic acid (mole ratio: 30:10:10) was introduced into the tube at the rate of 32 liters/hour. The reaction results are set forth in the following Table II.

Table II

| Sample No. | Production rate of vinyl acetate (g/l/hr.) | % Drop in activity** |
|---|---|---|
| 4-1 (control) | 98 | 28 |
| 4-2 | 132 | 7 |
| 4-3 | 149 | 5 |
| 4-4 | 158 | 0 |
| 4-5 | 150 | 0 |
| 4-6 | 141 | 5 |
| 4-7 (control) | 119 | 12 |

**Percent drop in activity =
$$\frac{\text{Activity during 2nd hour of reaction} - \text{activity after 90 days of reaction}}{\text{Activity during 2nd hour of reaction}} \times 100$$

EXAMPLE 3

Catalysts were prepared under the same conditions as described in Example 1 except that, instead of the alumina described in the Example 1, the various carriers indicated in Table III were employed. The resultant distribution patterns of palladium and gold are also shown in the Table III.

In the presence of 35 g. of each of these supported catalysts, vinyl acetate ws synthesized under the same reaction conditions as in Example 1. The reaction results are set forth in Table IV.

TABLE III

| No. | Carrier | Particle diameter of carrier (mm φ) | Surface area of carrier (m²/g) | Pore volume (cc/g) | Maximum peak radius (R) in pore radius distribution curve between 4 and 150 A; and the percentage of the sum of pore volumes between 0.5 R and 1.5 R relative to the total pore volume within the range of 4 to 750 A | | Distribution of palladium on carrier Distance from carrier surface as expressed in percentage of carrier particle radius | Distribution of gold on carrier Distance from carrier surface as expressed in percentage of carrier particle radius |
|---|---|---|---|---|---|---|---|---|
| 3-1 | Silica | 6 | 250 | 1.11 | 47 A | 75% | Within 20% (where 95% of palladium is present) | Within 20% (where 95% of gold is present) |
| 3-2 | Silica | 5 | 265 | 1.60 | 50 A | 73% | Within 18% (where 95% of palladium is present) | Within 18% (where 95% of gold is present) |
| 3-3 | Silica-alumina | Pellets, 4 × 6 | 59 | 1.44 | 170 A | 82% | Within 24% (where 95% of palladium is present) | Within 25% (where 95% of gold is present) |
| 3-4 | Silica | 6.5 | 120 | 0.65 | 245 A | 77% | Within 28% (where 95% of palladium is present) | Within 27% (where 95% of gold is present) |
| 3-5 | Silica | 5 | 241 | 0.94 | 85 A | 85% | Within 27% (where 95% of palladium is present) | Within 27% (where 95% of gold is present) |
| Control-1 | Silica | 4.5 | 89 | 1.25 | 320 A | 78% | Within 25% (where 95% of palladium is present) | Within 37% (where 95% of gold is present) |
| Control-2 | Silica | 6.5 | 255 | 0.84 | 92 A | 82% | Within 39% (where 95% of palladium is present) | Within 24% (where 95% of gold is present) |
| Control-3 | Silica-alumina | 5 | 115 | 1.22 | 130 A | 79% | Within 36% (where 95% of palladium is present) | Within 36% (where 95% of gold is present) |

Table IV

| Sample No. | Yield of vinyl acetate (g/l/hr.) |
|---|---|
| 3-1 | 183 |
| 3-2 | 190 |
| 3-3 | 168 |
| 3-4 | 183 |
| 3-5 | 189 |
| Control-1 | 134 |
| Control-2 | 136 |
| Control-3 | 128 |

In the samples Nos. 3-1 through 3-5, no loss of activity was observed over a 100-day period of reaction.

While the invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the following claims.

What is claimed is:

1. A method of producing vinyl acetate, which comprises reacting ethylene, oxygen and acetic acid, in vapor phase, in the presence of a catalyst comprising a particulate, porous carrier, at least predominantly comprised of a member selected from the group consisting of silica, alumina, and mixtures thereof supporting 0.3 to 3.0 percent by weight of palladium metal, 0.0157 to 1.8 percent by weight of gold metal, and 1 to 30 percent by weight of an alkali metal acetate, all based on the weight of said carrier, and wherein and on said carrier at least 90 percent by weight of each of the supported palladium and gold is distributed proximate the external surfaces of the carrier particles, extending to depths no greater than about 30% of particles radius as measured from the exterior surface to the center of such particles, said porous carrier has a particle radius 1.0 to 5.0 millimeters, a pore volume of 0.1 to 2.0 cubic centimeters per gram and an internal surface area of 10 to 350 square meters per gram.

2. The method of producing vinyl acetate as defined by claim 1, wherein the reaction is carried out at a temperature of from about 50° to 250° C. and a pressure in the range of from about atmospheric to 200 atmospheres.

3. The method of producing vinyl acetate as defined by claim 2, wherein said reaction is carried out at a temperature of from about 100° to 200° C. and a pressure in the range of from about atmospheric to 10 atmospheres.

4. The method of producing vinyl acetate as defined by claim 1, wherein the amount of gold metal supported is in the range of 5 to 60 percent by weight, based upon the combined weight of palladium and gold metal.

5. The method of producing vinyl acetate as defined by claim 1, wherein said porous carrier is a carrier wherein, with the maximum peak on its pore radius distribution curve being taken as R, the sum of pore volumes within the pore radius range of 0.5 to 1.5 R is not less than 60 percent of the total pore volume within the pore radius range of 4 to 750 angstrom units.

* * * * *